United States Patent
Tallarida et al.

(10) Patent No.: US 12,128,203 B2
(45) Date of Patent: *Oct. 29, 2024

(54) SEPTUM FOR ACCESS PORT

(71) Applicant: PRIMO MEDICAL GROUP, INC., Stoughton, MA (US)

(72) Inventors: Steven J. Tallarida, Mansfield, MA (US); John M. Butziger, East Greenwich, RI (US); Richard P. Rodgers, Hudson, MA (US)

(73) Assignee: PRIMO MEDICAL GROUP, INC., Stoughton, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/202,987

(22) Filed: May 29, 2023

(65) Prior Publication Data

US 2024/0157106 A1    May 16, 2024

Related U.S. Application Data

(63) Continuation of application No. 17/666,251, filed on Feb. 7, 2022, now Pat. No. 11,697,010, which is a
(Continued)

(51) Int. Cl.
*A61M 39/04*     (2006.01)
*A61M 39/02*     (2006.01)
*A61M 39/00*     (2006.01)

(52) U.S. Cl.
CPC ........ *A61M 39/04* (2013.01); *A61M 39/0208* (2013.01); *A61M 2039/0054* (2013.01);
(Continued)

(58) Field of Classification Search
CPC .............. A61M 39/04; A61M 39/0208; A61M 2039/0054; A61M 2039/0202; A61M 39/02–2039/047; A61M 2205/0205
See application file for complete search history.

(56) References Cited

U.S. PATENT DOCUMENTS 4,784,646 A * 11/1988 Feingold ........... A61M 39/0208
                                                          604/9
4,832,054 A    5/1989 Bark
(Continued)

FOREIGN PATENT DOCUMENTS

JP    S64500166 A    1/1989
JP    H02156962 A    6/1990
(Continued)

OTHER PUBLICATIONS

Examination Report from related Australian Application No. 2019224138, dated Nov. 14, 2023. 4 pages.
(Continued)

*Primary Examiner* — James D Ponton
*Assistant Examiner* — Hong-Van N Trinh
(74) *Attorney, Agent, or Firm* — Grossman, Tucker, Perreault & Pfleger, PLLC

(57) ABSTRACT

A medical device comprising an implantable subcutaneous access port having a septum penetrable by a needle; the septum having a cavity located between an outer wall and an inner wall, the cavity containing a flowable media comprising a plurality of displaceable particles arranged to move in response to the needle being inserted through the outer wall and into the cavity and reposition around the needle.

20 Claims, 3 Drawing Sheets

Related U.S. Application Data continuation of application No. 16/708,649, filed on Dec. 10, 2019, now Pat. No. 11,241,565, which is a continuation of application No. 15/642,941, filed on Jul. 6, 2017, now Pat. No. 10,512,766.

(60) Provisional application No. 62/359,422, filed on Jul. 7, 2016.

(52) U.S. Cl.
CPC . *A61M 2039/0205* (2013.01); *A61M 2202/06* (2013.01); *A61M 2205/0205* (2013.01); *A61M 2205/0216* (2013.01)

(56) References Cited

U.S. PATENT DOCUMENTS

| | | | | |
|---|---|---|---|---|
| 5,263,930 | A | * | 11/1993 | Ensminger ........ A61M 39/0606 604/288.03 |
| 5,476,460 | A | * | 12/1995 | Montalvo .......... A61M 39/0208 604/8 |
| 6,478,783 | B1 | | 11/2002 | Moorehead |
| 7,186,236 | B2 | | 3/2007 | Gibson et al. |
| 9,630,366 | B2 | | 4/2017 | Schuessler |
| 2007/0144539 | A1 | | 6/2007 | Van der Burg et al. |
| 2008/0027401 | A1 | * | 1/2008 | Ou-Yang ............ A61M 25/0017 604/265 |
| 2008/0172003 | A1 | * | 7/2008 | Plishka ................ A61M 39/26 604/249 |
| 2008/0195126 | A1 | | 8/2008 | Solem |
| 2009/0099529 | A1 | * | 4/2009 | Anderson ............. A61M 39/20 604/192 |
| 2011/0060407 | A1 | | 3/2011 | Ketai et al. |
| 2011/0265826 | A1 | | 11/2011 | Koehler |
| 2012/0109080 | A1 | | 5/2012 | Manesis et al. |
| 2014/0378942 | A1 | | 12/2014 | Christian et al. |
| 2015/0073547 | A1 | | 3/2015 | Eliasen et al. |
| 2015/0289976 | A1 | | 10/2015 | Machold et al. |
| 2020/0337840 | A1 | | 10/2020 | Reich |
| 2021/0015475 | A1 | | 1/2021 | Lau |

FOREIGN PATENT DOCUMENTS

| | | |
|---|---|---|
| WO | 8704631 A1 | 8/1987 |
| WO | 2018009635 A1 | 1/2018 |

OTHER PUBLICATIONS

Office Action from related Canadian Appln. No. 3,030,172, dated Sep. 21, 2023. 4 pages.
Office Action from related Japanese Appln. No. 2020-544829, dated Sep. 21, 2023. English translation attached.
Office Action from related Appln. No. 17824871.2, dated Nov. 27, 2023. 3 pages.
Office Action from related Appln. No. 17824871.2, dated Jan. 31, 2023. 5 pages.
Office Action from related U.S. Appl. No. 17/682,880, mailed Oct. 25, 2023. 16 pages.
Office Action from related U.S. Appl. No. 18/211,978, mailed Jun. 7, 2024. 10 pages.

* cited by examiner

SEPTUM FOR ACCESS PORT

CROSS-REFERENCE TO RELATED APPLICATIONS

This application is a continuation of U.S. patent application Ser. No. 17/666,251 filed Feb. 7, 2022, which is a continuation of U.S. patent application Ser. No. 16/708,649 filed Dec. 10, 2019, now U.S. Pat. No. 11,241,565, which is a continuation of U.S. patent application Ser. No. 15/642,941, filed Jul. 6, 2017, now U.S. Pat. No. 10,512,766, which claims the benefit of U.S. Provisional Patent Application Ser. No. 62/359,422, filed Jul. 7, 2016, all of which are incorporated herein by reference.

FIELD

The present disclosure relates to medical devices, and more particularly, an access port and septum thereof.

BACKGROUND

Once an implanted subcutaneous access port is located, a silicone septum of the port is typically pierced with a needle from outside the port. Generally a Huber needle, or a needle with a deflective, non-coring tip, is used to access a chamber of the port through the septum. The septum may be referred to as "self-sealing" or "resealable" given it is subject to multiple penetrations by the needle.

In order to inhibit undue septum damage and corresponding leakage, the needle size is ordinarily relatively small, in a range of 20-21 gauge. Even so, each entry by the needle may be understood to reduce the integrity of the septum. Further, a larger needle size is desirable, e.g. 14-17 gauge, to facilitate higher flow for fluids. However, large gauge hypodermic needles may further damage the septum of the implanted port.

SUMMARY

The present disclosure provides a septum, particularly for an access port, which may be less prone to damage by repeated needle insertions therein.

In at least one embodiment, the present disclosure provides a medical device comprising an access port having a septum penetrable by a needle; the septum having a cavity located between an outer wall and an inner wall, the cavity containing a flowable media comprising a plurality of displaceable particles arranged to move in response to the needle being inserted through the outer wall and into the cavity and reposition around the needle.

In at least one embodiment, each of the plurality of displaceable particles include an antimicrobial compound.

In at least one embodiment, the antimicrobial compound comprises at least one of a disinfectant, an antibiotic, an antibacterial, an antiviral and an antiparasitic.

In at least one embodiment, each of the plurality of displaceable particles are disposed in a gaseous medium. In at least one embodiment, the gaseous medium comprises nitrogen gas.

In at least one embodiment, each of the plurality of displaceable particles are disposed in a liquid medium.

In at least one embodiment, the liquid medium comprises at least one of an antimicrobial compound and a sealing compound to seal the cavity in response to penetration by the needle.

In at least one embodiment, each of the plurality of displaceable particles are substantially spherical.

In at least one embodiment, each of the plurality of displaceable particles has dimensional size of at least 0.018 inch.

In at least one embodiment, each the plurality of displaceable particles has an outer coating.

In at least one embodiment, the outer coating comprises at least one of an antimicrobial compound and a sealing compound to seal around the needle in response to penetration of the needle into the cavity.

In at least one embodiment, each the plurality of displaceable particles are at least one of deformable and compressible.

In at least one embodiment, each of the plurality of displaceable particles is formed of plastic.

In at least one embodiment, the plurality of displaceable particles comprises at least two different shaped particles.

In at least one embodiment, the plurality of displaceable particles comprises at least two different sized particles.

In at least one embodiment, the septum overlies a chamber within the access port; and the chamber is in fluid communication with a lumen of a catheter.

In at least one embodiment, the septum is formed of plastic, particularly an elastomer such as silicone.

In at least one embodiment, the present disclosure provides a method of operating a medical device, comprising inserting a needle into a septum of an implantable subcutaneous access port such that the needle displaces a plurality of particles of a particulate media within the septum as the needle is inserted into the septum; inserting the needle through the septum and into a chamber of the access port beneath the septum; and at least one of delivering and removing fluid from the chamber of the access port through the needle.

FIGURES

The above-mentioned and other features of this disclosure, and the manner of attaining them, will become more apparent and better understood by reference to the following description of embodiments described herein taken in conjunction with the accompanying drawings, wherein.

DETAILED DESCRIPTION

Figure 1:
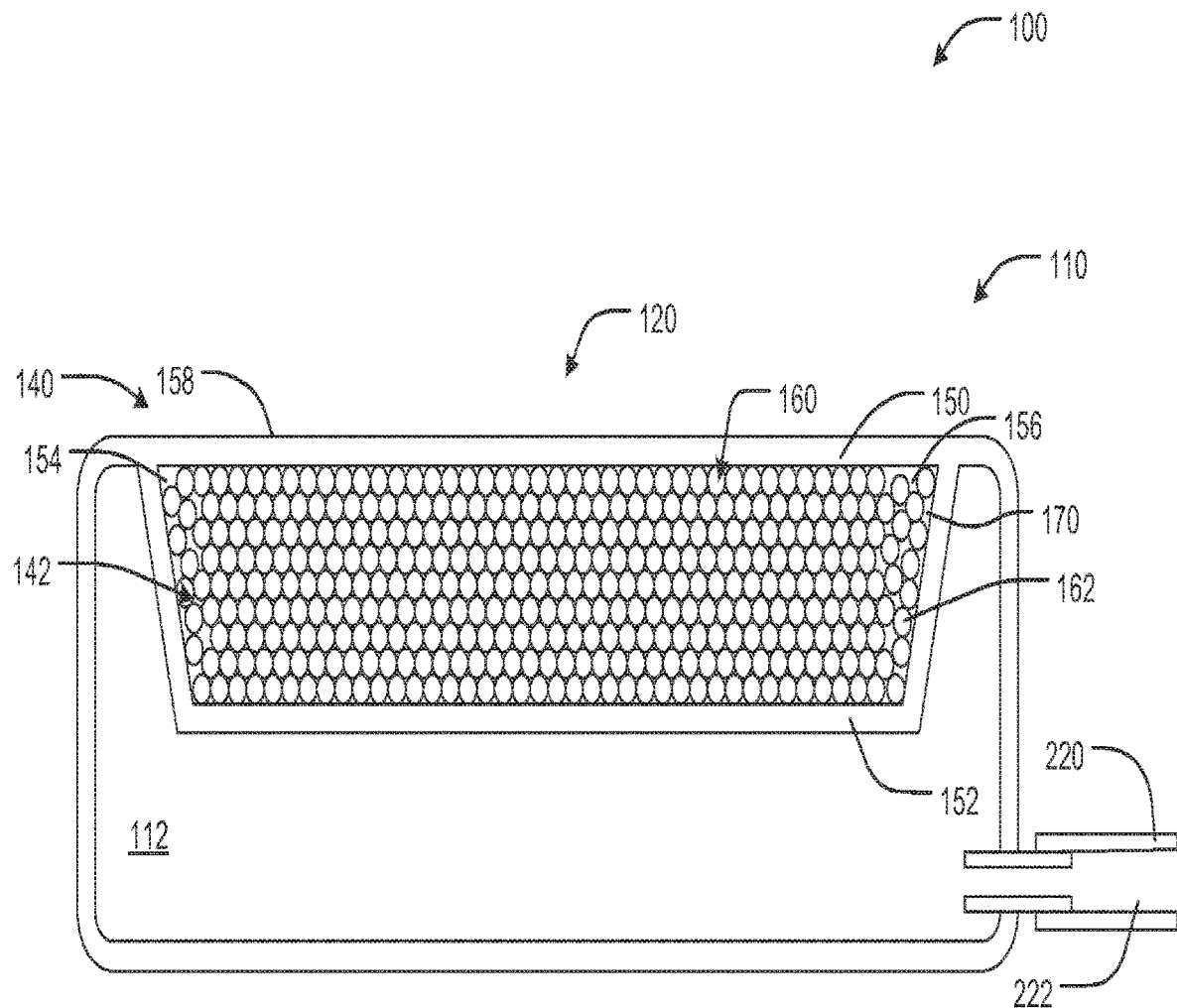
FIG. 1 is a cross-sectional view of an access port including an access port septum according to the present disclosure.

It may be appreciated that the present disclosure is not limited in its application to the details of construction and the arrangement of components set forth in the following description or illustrated in the drawings. The invention(s) herein may be capable of other embodiments and of being practiced or being carried out in various ways. Also, it may be appreciated that the phraseology and terminology used herein is for the purpose of description and should not be regarded as limiting as such may be understood by one of skill in the art.

Figure 2:
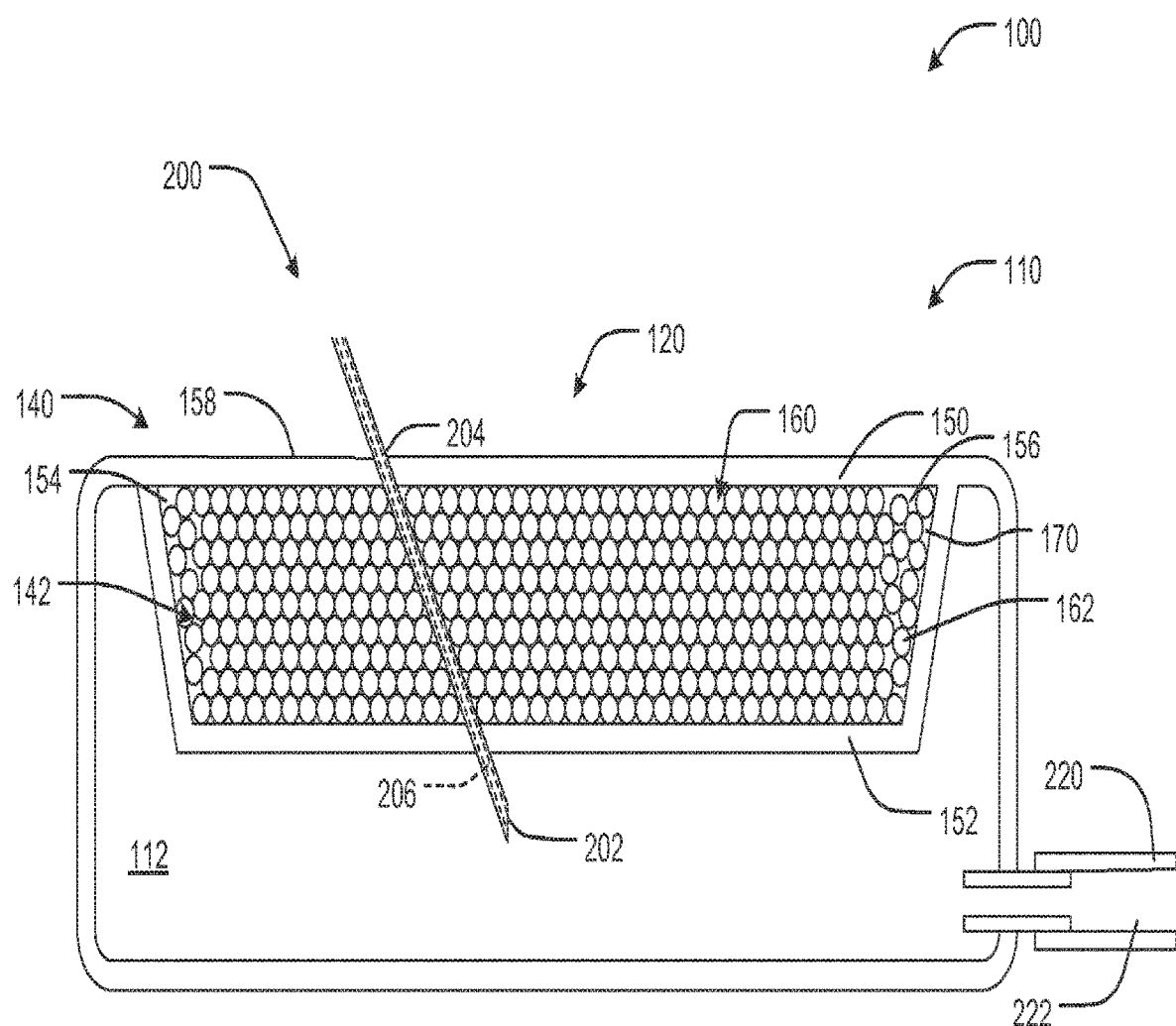
FIG. 2 is a cross-sectional view of the access port including the access port septum of FIG. 1 penetrated by a needle.

Referring now to FIGS. 1 and 2, there is shown a medical device, particularly an an implantable (subcutaneous) access port 100 which comprises an access port body 110 and a septum 120 within the access port body 110, which is penetrable by needle 200 (such as a non-coring needle (e.g. Huber), having an inner core 142 contained within a deformable outer shell 140. Outer shell 140 may comprise an outer wall layer 150 and an inner wall layer 152 defining a sealed cavity 154 which contains the core 142. The outer shell 140, and more particularly outer wall layer 150 and inner wall layer 152, may be formed of a flexible, self-sealing (resealable) resilient elastomer (e.g. silicone; rubber; PTFE/silicone mixture; PTFE/rubber mixture) composition suitable for multiple penetrations. The outer surface 158 of outer wall layer 150 may be coated with an antimicrobial compound to kill microorganisms, which may comprise at least one of a disinfectant, an antibiotic, an antibacterial, an antiviral and an antiparasitic.

In light of the septum 120 being formed of a flexible/deformable composition, it may be understood that the cavity 154 may be deformable, with deformation of the outer flexible shell 140, particularly resulting from insertion of the needle 200. The cavity 154 formed by the outer shell 140 may be at least partially filled (e.g. at least 50% filled by volume) with a flowable media 160 to provide the core 142, and more particularly substantially filled with the flowable media 160 (e.g. at least 75% filled by volume and more particularly at least 85% filled by volume).

Media 160 may comprise a particulate of displaceable particles 162 arranged to move in response to the needle 200 being inserted through the outer wall layer 150 and into the cavity 154. In such regard, the displaceable particles 162 may be understood to be free-flowing, i.e. particles which are not attached to anything and able to move freely around one another and do not substantially cohesively bond to one another to form aggregates. In the present embodiment, the remainder of the cavity 154, such as the interstices 156 between the particles 162 may be filled with a gaseous medium, such as nitrogen gas under atmospheric pressure. While the particles 162 may be shown to have an ordered pattern in the medial region of the core 142, the particles 162 may exhibit any pattern, random or ordered.

Referring now to FIG. 2, due to the flowability of the media 160, including particles 162, as a needle 200 is inserted and penetrates through the outer wall layer 150 of the shell 140 and through the particles 162 of the core 142 within cavity 154, the particles 162 adjacent the distal end tip 202 of the needle 200 move to accommodate the insertion path of the needle 200 through the outer wall layer 150 and into the cavity 154 and flow (reposition) around the shaft 204 of the needle 200. This may enhance the seal provided by the outer wall layer 150 of the septum 120. With continued insertion, the needle 200 may then penetrate through the inner wall layer 152 of the outer shell 140 and into a fluid chamber 112 of the access port 100 where the needle 200 would be in fluid communication with the chamber 112 and lumen 222 of attached catheter 220. The needle 200 may then be used to deliver fluid (liquid) into the fluid chamber 112 into the lumen 222 of attached catheter 220 and into the host (e.g. patient), or alternatively the needle 200 may then be used to remove fluid (liquid) from the fluid chamber 112 from the lumen 222 of attached catheter 220 and from the host (e.g. patient). The needles 200 contemplated herein may have gauge sizes in a range of 12 gauge to 21 gauge (e.g. 12, 13, 14, 15, 16, 17, 18, 19, 20, 21 or 22 gauge), and any range therein.

Figure 3A:
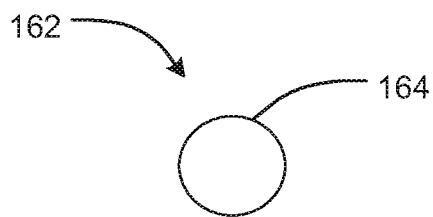
FIG. 3A is an exemplary particle according to the present disclosure.

Referring to FIG. 3A, in order to inhibit microorganisms from entering the septum 120, the particles 162 may each include an antimicrobial compound, which may be provided as a coating on the outer surface 164 of the particles 162. The antimicrobial compound may comprise at least one of a disinfectant, an antibiotic, an antibacterial, an antiviral and an antiparasitic. The coating may also include a sealing compound to seal around the needle 200 in response to penetration of the needle 200 into the cavity 154.

In other embodiments, the media 160 within cavity 154 may also comprise a liquid medium 170 which occupies the interstices 156 between the particles 162. The liquid medium may include at least one of an antimicrobial compound, and a sealing compound to seal the cavity 154 in response to penetration by the needle 200. In such regard, the core 142 may be considered a composite material comprising a discontinuous phase (i.e. particles 162) dispersed in a continuous phase (i.e. liquid 170).

Referring again to FIG. 3A, the media particles 162 may be at least substantially spherical, such as that of a spheroid, which may be understood as an ellipsoid that approximates a sphere. As used herein, a particle 162 may also be considered substantially spherical if the difference in length between its major axis and its minor axis is less than 20%, and more particularly less than 10%. The particles 162 may also be perfectly spherical (i.e. the length of the major axis and the minor axis is the same).

Figure 3B:
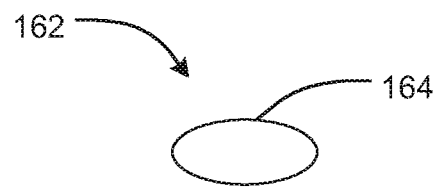
FIG. 3B is an exemplary particle according to the present disclosure.
Figure 3C:
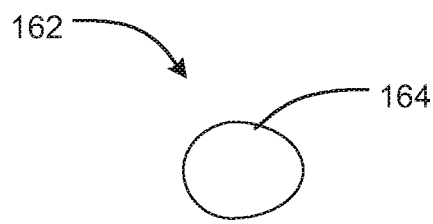
FIG. 3C is an exemplary particle according to the present disclosure.
Figure 3D:
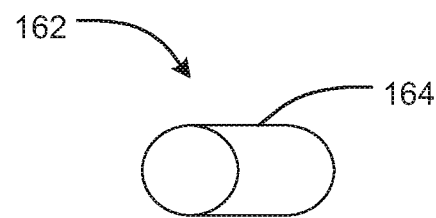
FIG. 3D is an exemplary particle according to the present disclosure.

Other than being at least substantially spherical, the particles 162 may have other shapes such as oval/oblong as shown in FIG. 3B, egg shaped as shown in FIG. 3C or cylindrical as shown in FIG. 3D. The particles 162 making up the particulate may all have the same shape, or the particles 162 may have two or more different shapes, such as a combination of spherical and cylindrical (i.e. a mixed shape particles). The particles 162 making up the particulate may all have the same size, or the particles 162 may have two or more different sizes, such as a combination of small, medium (intermediate) and large particles, or microscopic and macroscopic particles (i.e. mixed sized particles). The particles 162 making up the particulate may also have at least two different shapes and at least two different sizes.

The particles 162 should have a dimensional size larger than an inner diameter of the needle, i.e. a dimensional size larger than the diameter of the lumen 206 of the needle 200 and distal end opening, so that the particles 162 may not enter the needle 200 and occlude the needle lumen or distal end opening.

The particles 162 may have a dimensional size (e.g. diameter) at least 5% larger than the diameter of the lumen 206 of the needle 200 to be used, more particularly at least 10% larger than the diameter of the needle to be used, and more particularly at least 15% larger than the diameter of the needle to be used.

By way of example, to use a needle size having a gauge of 22 or smaller, the particles 162 may have a dimensional size (e.g. cross-sectional length such as diameter) of at least 0.018 inch (stated another way, not less than 0.018 inch), and more particularly at least 0.028 inch. For a needle size having a gauge of 21 or smaller, the particles 162 may have a dimensional size (e.g. diameter) of at least 0.022 inch, and more particularly at least 0.032 inch. For a needle size having a gauge of 20 or smaller, the particles 162 may have a dimensional size (e.g. diameter) of at least 0.026 inch, and more particularly at least 0.036 inch. For a needle size having a gauge of 19 or smaller, the particles 162 may have a dimensional size (e.g. diameter) of at least 0.030 inch, and more particularly at least 0.040 inch. For a needle size having a gauge of 18 or smaller, the particles 162 may have a dimensional size (e.g. diameter) of at least 0.036 inch, and more particularly at least 0.046 inch. For a needle size having a gauge of 17 or smaller, the particles 162 may have a dimensional size (e.g. diameter) of at least 0.045 inch, and more particularly at least 0.055 inch. For a needle size having a gauge of 16 or smaller, the particles 162 may have a dimensional size (e.g. diameter) of at least 0.050 inch, and more particularly at least 0.060 inch. For a needle size having a gauge of 15 or smaller, the particles 162 may have a dimensional size (e.g. diameter) of at least 0.057 inch, and more particularly at least 0.067 inch. For a needle size having a gauge of 14 or smaller, the particles 162 may have a dimensional size (e.g. diameter) of at least 0.067 inch, and more particularly at least 0.077 inch.

Figure 3E:
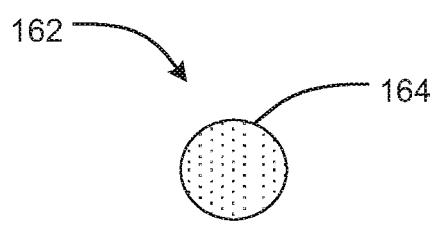
FIG. 3E is an exemplary particle according to the present disclosure.
Figure 3F:
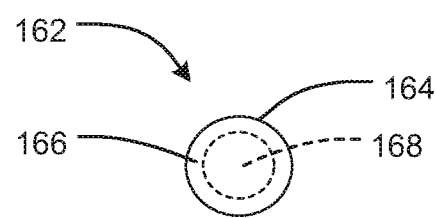
FIG. 3F is an exemplary particle according to the present disclosure.
Figure 3G:
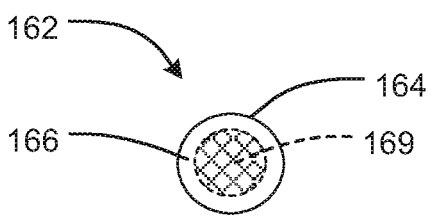
FIG. 3G is an exemplary particle according to the present disclosure.

In certain embodiments, the particles 162 may comprise, essentially consist of or consist of plastic, ceramic and metal. In certain embodiments, the particles 162 may have a solid (FIG. 3A) or porous wall structure, e.g. foamed such as shown in FIG. 3E. In certain embodiments, the particles 162 may have a hollow interior cavity 168 within an outer shell 166 as shown in FIG. 3F. In certain embodiments, the plurality of displaceable particles may have an outer shell 166 encapsulating an inner core 169 as shown in FIG. 3G. The inner core 169 may comprise at least one of an antimicrobial compound and a sealing compound to seal the cavity in response to penetration of the needle into the cavity 154, in the event the particle 162 is pierced.

Particles 162 formed of plastic, and more particularly an elastomer, may be resiliently deformable and/or compressible under the force/pressure generated by insertion of the needle 200 such that the particles 162 deform around and against the needle to provide a seal.

Particles 162 formed of plastic, and more particularly a foam (FIG. 3E) and/or being hollow (FIG. 3F), may be resiliently deformable and/or compressible under the force/pressure generated by insertion of the needle 200 such that the particles 162 deform around and against the needle to provide a seal.

Inner core 169 may be formed of a liquid to make the particle 162 more resiliently deformable and/or compressible under the force/pressure generated by insertion of the needle 200 such that the particles 162 deform around and against the needle to provide a seal.

Unlike conventional self-sealing silicone septums, where the septum may be expected to ultimately fragment due to repeated needle insertion and associated cutting of the silicone, the flowable ability of the particles 162 allows the particles 162 to displace during insertion of the needle 200 such that the particles 162 are not damaged by the needle 200. In addition, the flowability of the particles 162 permits them to fill in the path of the needle 200 when the needle 200 is removed from the septum 120. Further, particles 162 creates a tortuous flow path that prevents undue ingress of any fluid or organic material. The repositioning of the particles 162 with each needle stick may also inhibit biologic growth by discontinuing any contiguous biologic colonies.

While a preferred embodiment of the present invention(s) has been described, it should be understood that various changes, adaptations and modifications can be made therein without departing from the spirit of the invention(s) and the scope of the appended claims. The scope of the invention(s) should, therefore, be determined not with reference to the above description, but instead should be determined with reference to the appended claims along with their full scope of equivalents. Furthermore, it should be understood that the appended claims do not necessarily comprise the broadest scope of the invention(s) which the applicant is entitled to claim, or the only manner(s) in which the invention(s) may be claimed, or that all recited features are necessary.

LIST OF REFERENCE CHARACTERS 100 access port
110 access port body
112 chamber
120 access port septum
140 outer shell
142 inner core
150 outer wall layer
152 inner wall layer
154 cavity
156 interstices
158 outer surface
160 media
162 particles
164 outer surface
166 outer shell
168 inner cavity
169 inner core
170 fluid (liquid)
200 tubular penetrating member/needle
202 tip
204 shaft
206 lumen
220 catheter
222 lumen

What is claimed is:

1. A medical device comprising:
an implantable subcutaneous access port having a septum penetrable by a needle;
the septum having a cavity located between an outer wall and an inner wall, the cavity containing a flowable media comprising a plurality of displaceable particles arranged to move in response to the needle being inserted through the outer wall and into the cavity and reposition around the needle;
wherein at least the outer wall is self-sealing in response to withdrawal of the needle therefrom; and
wherein each of the plurality of displaceable particles comprises an antimicrobial compound.

2. The medical device of claim 1 wherein:
wherein each of the plurality of displaceable particles has a dimensional size of at least 0.018 inch.

3. The medical device of claim 1 wherein:
the antimicrobial compound comprises at least one of a disinfectant, an antibiotic, an antibacterial, an antiviral and an antiparasitic.

4. The medical device of claim 1 wherein:
each of the plurality of displaceable particles of the flowable media are disposed in a gaseous medium.

5. The medical device of claim 4 wherein:
the gaseous medium comprises nitrogen gas.

6. The medical device of claim 1 wherein:
each of the plurality of displaceable particles of the flowable media are disposed in a liquid medium.

7. The medical device of claim 6 wherein:
the liquid medium comprises an antimicrobial compound.
8. The medical device of claim 1 wherein:
each of the plurality of displaceable particles are substantially spherical.
9. The medical device of claim 1 wherein:
each the plurality of displaceable particles has an outer coating.
10. The medical device of claim 9 wherein:
the outer coating comprises the antimicrobial compound.
11. The medical device of claim 1 wherein:
each the plurality of displaceable particles are deformable and/or compressible.
12. The medical device of claim 1 wherein:
each of the plurality of displaceable particles is formed of plastic, metal, ceramic or a combination thereof.
13. The medical device of claim 1 wherein:
the plurality of displaceable particles comprises at least two different shaped particles.
14. The medical device of claim 1 wherein:
the plurality of displaceable particles comprises at least two different sized particles.
15. The medical device of claim 1 wherein:
the septum overlies a chamber within the implantable subcutaneous access port; and
the chamber is in fluid communication with a lumen of a catheter.
16. The medical device of claim 1 wherein:
the septum is formed of plastic.
17. The medical device of claim 1 wherein:
the septum is formed of an elastomer.
18. The medical device of claim 1 wherein:
the septum is formed of silicone.
19. The medical device of claim 1 wherein:
the outer wall and the inner wall are provided by a one-piece body which defines a sealed cavity.
20. A medical device comprising:
an implantable subcutaneous access port having a septum penetrable by a needle;
the septum having a sealed cavity located between an outer wall and an inner wall, the sealed cavity containing a flowable media comprising a plurality of displaceable particles arranged to move in response to the needle being inserted through the outer wall and into the sealed cavity and reposition around the needle;
wherein at least the outer wall is self-sealing in response to withdrawal of the needle therefrom; and
each of the plurality of displaceable particles are substantially spherical.

* * * * *